United States Patent [19]
Suzuki et al.

[11] Patent Number: 5,929,224
[45] Date of Patent: Jul. 27, 1999

[54] LEUKOCYTE CELL—DERIVED CHEMOTAXIN 2B (LECT2B)

[75] Inventors: Kazuo Suzuki, 663-2, Shiigi, Misaki-machi, Isumi-gun, Chiba-ken; Satoshi Yamagoe, Kashiwa; Yoshio Yamakawa, Nagareyama; Satoshi Mizuno, Funabashi, all of Japan

[73] Assignee: Kazuo Suzuki, Chiba-ken, Japan

[21] Appl. No.: 08/563,148

[22] Filed: Nov. 27, 1995

[30] Foreign Application Priority Data

Nov. 28, 1994 [JP] Japan .................................. 6-293233

[51] Int. Cl.⁶ ............................. C12N 15/12; C12N 1/21; C12N 5/10; C12N 15/62
[52] U.S. Cl. .................... 536/23.5; 536/23.4; 435/320.1; 435/252.3; 435/325
[58] Field of Search .................... 536/23.1, 23.5, 536/24.1, 23.51, 23.4; 435/320.1, 172.3, 69.1, 69.5, 252.3, 325, 254.2, 348, 352, 354, 360, 363, 364, 365.1, 366, 367

[56] References Cited

U.S. PATENT DOCUMENTS

| | | | |
|---|---|---|---|
| 5,324,638 | 6/1994 | Tao et al. ................................ | 435/69.1 |
| 5,532,142 | 7/1996 | Johnston et al. ........................ | 435/69.1 |
| 5,583,107 | 12/1996 | Wolf et al. ................................ | 514/12 |
| 5,593,866 | 1/1997 | Hancock et al. ........................ | 435/69.7 |
| 5,612,209 | 3/1997 | King ......................................... | 435/198 |

OTHER PUBLICATIONS

Tomizawa et al. Nippon Bunshi Seibutsu Gakkai Nenkai Puroguramu, Koen Yoshishu 17:416. Conference Abstract, 1994.

*Primary Examiner*—Elizabeth Kemmerer
*Attorney, Agent, or Firm*—Jordan and Hamburg LLP

[57] ABSTRACT

Human LECT2a polypeptide having amino acid sequence in the order shown in Sequence ID NOs. from 1 to 5, which did not include other proteins/peptides and human LECT2b polypeptide having amino acid sequence in the order shown Sequence ID NO. 6 in which did not include other proteins/peptides, and DNA coding LECT2b sequence.

8 Claims, 1 Drawing Sheet

LEUKOCYTE CELL— DERIVED CHEMOTAXIN 2B (LECT2B)

BACKGROUND OF THE INVENTION

1. Field of the Invention

This invention is concerned with structures of novel human leukocyte activating proteins and DNA encoding the protein. The invention is also concerned with recombinant plasmids and the transformants.

2. Prior art

Neutrophils migrate in response to increasing concentrations of chemotactic factors released from inflammatory sites. Activated neutrophils are recruited from the blood through the vessel wall to the infected site, and phagocytize invading bacteria or viruses. The phagosomes fuse with lysosomes, and the lysosomal enzymes and active oxygen radicals kill the invaders. Thus, the chemotactic factors released from inflammatory sites play an important role in activating neutrophil functions. After reaction by neutrophils in acute inflammation, monocytes and lymphocytes are involved in the immune response. In addition to other immune cells including cytotoxic lymphocytes, NK cells and macrophages, neutrophils exhibit a cytotoxic activity against tumor cells in vitro. In their tumorcidal actions, immune cells also migrate to tumor-growing sites, suggesting that tumor cells also produce a chemotactic factor for the immune cells. In this regard, it has been demonstrated that neoplastic cells of mouse and human origin produce chemotactic factors which mediate macrophage infiltration into tumor tissues. We have also identified LUCT/IL-8, which has been constitutively secreted from the carcinoma cell line LU65C (K. Suzuki et al., J. Exp. Med., 169, 1895–1901, 1989). The cells were established from human lung carcinoma tissue infiltrated by many neutrophils. The myeloid leukemia cell line ML-1 and glioma cells also produce LUCT/IL-8 constitutively (K. Suzuki et al., Immunol. Lett. 36, 71–82, 1993). The culture fluids of 97 human leukemia cell lines have been screened to search for a novel chemotactic protein. As a result, this invention has been produced.

Neutrophils seem to damage cancer cells in addition to macrophages and lymphocytes. Moreover, some histological tissues of cancer tissues are infiltrated with neutrophils. These are believed to be neutrophils response to chemotactic factors secreted from cells in these tissues.

Secretion of interleukins and damage of tumor cells are induced by activation of neutrophils, macrophages and lymphocytes. Thus, both natural and acquired immunities are enhanced. When the leukocyte activating factors are purified with large scale and simple procedures, those are used for diagnosis, therapy and determination after treatment. Further, these are also useful for basic research in activating mechanisms of neutrophils, macrophages and lymphocytes. We have found a neutrophil chemotactic factor, interleukin 8 (LUCT/IL-8) from culture fluid of cells established from human giant carcinoma cells. Then, we purified the factor (protein) and cloned the gene. IL-8 is about 8-kDa plain protein with pI 10.3. Two kinds of protein, 77-amino acid protein and 72-amino acid-protein are classified in IL-8, and possess the chemotactic activities with the same specific activity. Furthermore, IL-8 is a cytokine of inflammation and is detected in the serum of patients with chronic inflammation.

However, it has been thought that neutrophil chemotactic factor different from IL-8 is related with interaction between neutrophils and cancer cells.

SUMMARY OF THE INVENTION

The culture fluids of 97 human leukemia cell lines have been screened to search for a novel chemotactic protein. The neutrophil chemotactic protein was detected in a culture fluid of the PHA-activated human T-cell leukemia cell line SKW-3. The protein was purified and its molecular size was determined with sodium dodecyl sulfate (SDS)polyacryl amide gel electrophoresis (PAGE) as 16 kDa, which is double the size compared with that of IL-8. The amino acid sequence analysis revealed that the chemotactic protein is a novel protein, which is designated LECT2a (leukocyte cell-derived chemotaxin 2a). Furthermore, cloning of LECT2a cDNA by polymerase chain reaction (PCR) based on the partial amino acid sequences was carried out. Then, cDNA encoding a protein which had higher homology with LECT2a was isolated. The encoded protein was designated LECT2b.

These results show that the neutrophil activating factor LECT2 involves two kinds of LECT2a and LECT2b proteins, which are identical in leukocyte activation, but different from each other in their amino acid sequences. Comparison of the amino acid sequence of LECT2a with that deduced from cDNA encoding LECT2b indicates 86% homologous sequence. The amino acid sequences of LECT2a are shown in Sequence ID NO. 1 to in the order from N-terminus. The deduced amino acid sequence of LECT2b is shown in Sequence ID NO. 6 in the order from N-terminus. Sequence ID NO. 7 shows both cDNA nucleotide sequence and deduced amino acid sequence of LECT2b. Amino acid number 58 Val in the Sequence ID NOs. 6 and 7 can be replaced with Ile. Then, CTC in the nucleotide Sequence ID No. 372–374 is ATC. It seems to be due to polymorphism in individuals. When amino acid sequences of LECT2a and LECT2b are compared with each other, there are significant overlaps therebetween. Blank sequence of LECT2a is believed to be higher homology with that of LECT2b, because that molecular size 16 kDa and amino acid component are almost the same.

Leukocyte activating factors in this invention are human LECT2 polypeptides having sequences in Sequence ID NOs. 1–5 or the sequence in Sequence ID NO. 6 in the sequence listing.

This invention is also concerned with genomic DNA which encodes human LECT2b having the amino acid sequence in Sequence ID NO. 6 in the Sequence Listing. Especially, a nucleotide sequence is concerned with the genomic DNA sequence shown in Sequence ID NO. 7 in the Sequence Listing.

This invention is also concerned with the recombinant plasmid encoding human LECT2b having the amino acid sequence in Sequence ID NO. 6 in the Sequence Listing. The invention is also concerned with plasmid pMAL-TEV-LECT2b producing fusion protein. The nucleotide sequence encoding LECT2b protein was ligated down-stream of the maltose-binding protein region in pMAL-c vector. Then, the fused protein can be induced by isopropyl-$\beta$-D-thiogalactopyranoside (IPTG) treatment. This construct has a TEV protease recognition site which is located between the maltose-binding protein and LECT2b. The plasmid pMAL-TEV-LECT2b can be obtained from E. coli Mal-LECT2b strain (deposited at the NATIONAL INSTITUTE OF BIOSCIENCE AND HUMAN-TECHNOLOGY, Agency of Industrial Science and Technology, 1-3, Higashi 1-chome, Tsukuba-shi, Ibaraki-ken 305, Japan under FERM P-14669 and transferred to international deposition under FERM BP-5302 on Nov. 24, 1995 under the Budapest Treaty). The nucleotide sequence encoding LECT2b protein was ligated down-stream of the glutathione-S-transferase region in pGEX-3X vector. Production of the fused protein can be induced by IPTG treatment. This construct has a Xa protease recognition site located between glutathione-S-transferase and LECT2b. The invention is also concerned with recombinant plasmid DNA encoding human LECT2b regulated with SRalpha promotor, which can highly express LECT2b.

The invention is also concerned with transformed cells, especially ones obtained by transforming into E. coli, yeast, insect cells, animal cells such as chinese hamster CHO cells, monkey CVI cells, monkey CVI/293 cells, mouse fibroblast cells, mouse C127 cells, mouse 3T3 cells, mouse L-929 cells, human HeLa cells and human SKW-3 cells, which can express the recombinant plasmid encoding human LECT2b having the amino acid sequence in Sequence ID No. 6 in the Sequence Listing.

DETAILED DESCRIPTION OF THE INVENTION

Figure 1:
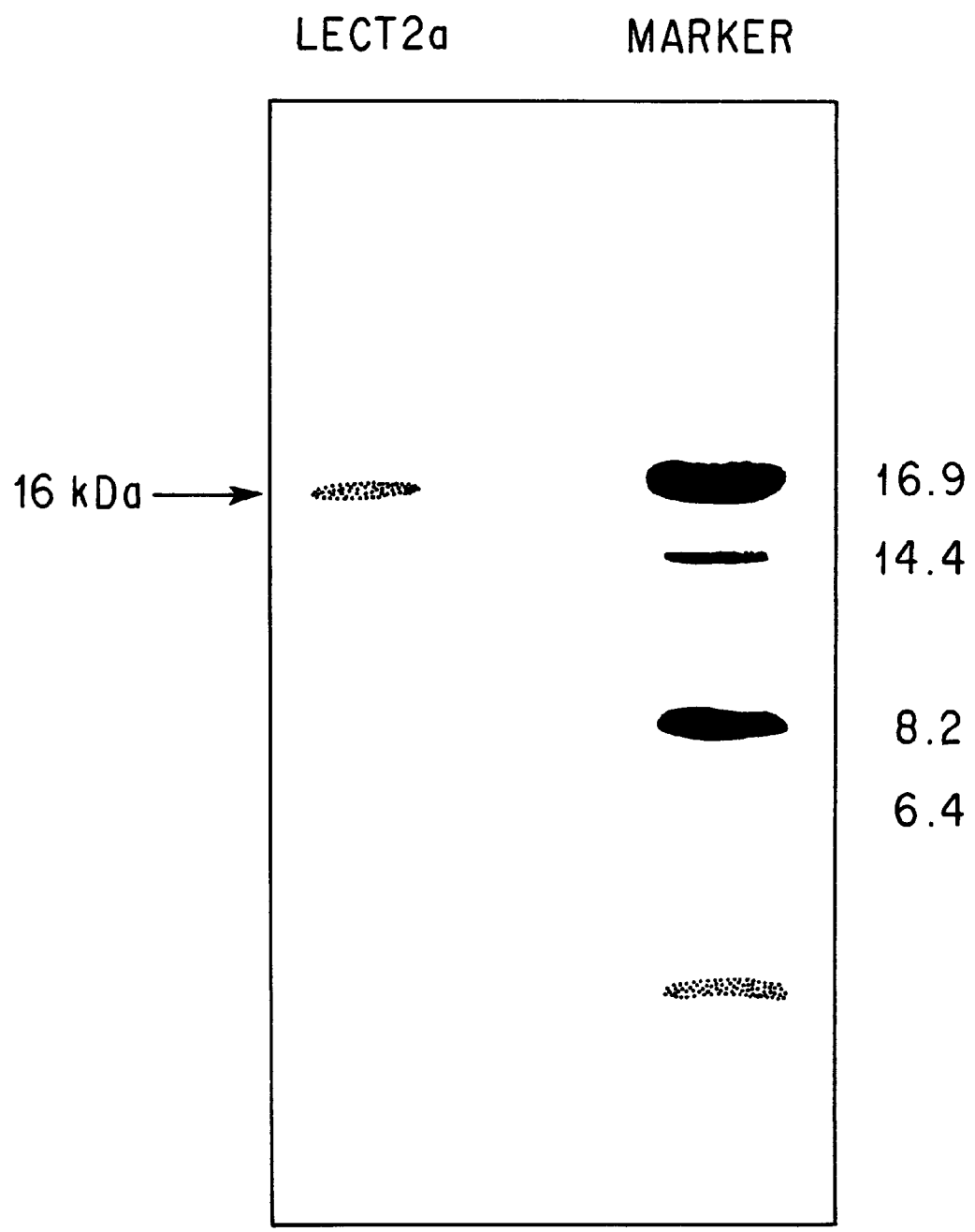
FIG. 1 shows how the molecular size of LECT2a, and of LECT2a was determined by Tricin-SDS-PAGE with 16.5% monoacrylamide-bisacrylamide: 3% bis/monoacrylamide containing bis.

Leukocyte activation indicates functions of neutrophils, monocytes (macrophages), and lymphocytes. The functions of neutrophils and monocytes (macrophages) are as follows: adhesion, migration (chemotaxis), phagocytosis, superoxide production, release of lysosomal proteins/enzymes (degranulation), cellular killing involving tumoricidal activity and production of various cytokines. The functions of lymphocytes are as follows: secretion of immunoglobulins, various cytokines, and expression of various receptors.

The neutrophil activating protein can be purified from a culture fluid of leukemia cells by concent ration with CM-Sepharose (trade name, available from Pharmacia Biotech, Uppsala, Sweden) and DEAE-Sepharose (trade name, available from Pharmacia Biotech, Uppsala, Sweden), CM-Sepharose column chromatography, hydroxylapatide chromatography on high performance liquid chromatography (HPLC), and reversed-phase column chromatography on HPLC. For example, SKW-3 cells were maintained in RPMI-1640 medium (trade name, available from GIBCO BRL, Grand Island, N.Y.) supplemented with 10% fetal calf serum (FCS) (available from GIBCO BRL). SKW-3 cells and other leukemia cells were stimulated with PHA-P (trade name, available from DIFCO Laboratories, Detroit, Mich.) and the leukocytes activating factor described in the invention can be purified from this culture fluid using column chromatography etc.

In addition, the neutrophil activating factor can be produced by the transfomant with the recombinant plasmid of the factor. The recombinant plasmid can be constructed with a vector, for example, pMAL-c (trade name, available from Biolab Inc.) or pGEX-3X (trade name, available from Pharmacia Inc.). Animal cells, yeast, and bacteria can be used as transformed cells, for example, chinese hamster CHO cells, monkey CVI cells, monkey CVI/293 cells, mouse fibroblast cells, mouse C127 cells, mouse 3T3 cells, mouse L-929 cells, human HeLa cells and human SKW-3 cells. Cell culture, purification of these activating proteins, construction of recombinant plasmids, transformation, and purification of the protein from the transformant are carried out by common procedures.

EXAMPLES

Explanation of a practical example is shown below.
1. Procedures for purification of LECT2a Materials used include:
   1) 1% bovine serum albumin (BSA, available from Diagnostics, Kankakee, Ill.) in deionized and distilled water (DDW).
   2) R buffer: 50 mM sodium phosphate buffer, pH 7.4.
   3) R5 buffer: R buffer containing 0.005% BSA.
      R1 buffer: R buffer containing 0.001% BSA.
   4) CM elution buffer: R1 buffer containing 0.7 M NaCl.
1) SKW-3 cells were cultured for 24 hours at 37° C. in a 5% $CO_2$ incubator in a 500-ml glass spinner culture bottle (available from GIBCO BRL) in the presence of PHA-P at a concentration of 5 μg/ml. The culture fluid was harvested by centrifugation at 400×g for 15 min at 4° C. The supernatant (7 liters) of the culture fluid was divided into 500-ml aliquots and stored at −80° C.
2) Cold DDW (20 liters) was added into the frozen supernatant (7 liters) to thaw the sample. The sample was used for purification of the leukocyte activating factor described in the invention.
Partial Purification of LECT2a
1) After the culture fluid was thawed, it was mixed with 200 ml of CM-Sepharose CL-6B (available from Pharmacia Biotech, Uppsala, Sweden) equilibrated with R1 (100 ml packed volume).
2) The mixture was stirred for 4 hours at 4° C.
3) It was filtered through a "KIRIYAMAROHTO SU-95" funnel (trade name, available from Kiriyama, Tokyo, Japan) with 3 sheets of filter paper No. 5B (95 mm in diameter; available from Kiriyama).
4) CM-Sepharose gel was washed sequentially with 500 ml of cold DDW.
5) Then, it was washed twice with 100 ml of R5.
6) The gel was slowly eluted with 50 ml of R5 supplemented with 0.7 M NaCl.
7) This elution was repeated 6 times.
8) The combined eluent was dialyzed against R using Spectra/Por 3 (trade name, available from Spectrum, Houston, Tex.) which had been rinsed with R5.
9) A DEAE-Sepharose (trade name, available from Pharmacia Biotech) suspension (12 ml packed volume) equilibrated with R5 was added to the dialysate.
10) The mixture was stirred for 2 hours at 4° C.
11) And then it was filtered through a "KIRIYAMAROHTO SU-95" funnel with 3 sheets of R5-rinsed filter paper No. 5B (95 mm in a diameter).
12) The gel was washed with 25 ml of cold R5.
13) The pass-through fraction of the DEAE-Sepharose was applied again to the second CM-Sepharose column equilibrated with R5 (3 ml packed volume in an Econo Column, trade name, available from Bio-Rad Laboratories, Tokyo, Japan).
14) The column was eluted using a linear gradient of 10 ml of R1 buffer and 10 ml of R1 buffer containing 0.7 M NaCl at 4° C. at a flow rate of 10 ml/hour.
15) Fractions containing chemotactic activity (Nos. 8–11) were used for partial purified principle.
Complete Purification With Column chromatography on HPLC
1) The purified samples, which were repeated two times, were combined.
2) The combined sample (2.5 ml, 1.2 O.D.) containing neutrophil-chemotactic activity was applied to a reverse-phase column (trade name, available from Vydac C4 column 304-2151, 4.5×250 mm) on HPLC.

3) The column was eluted with 22.5% to 60% acetonitrile containing 0.1% tetrafluoroacetic acid (TFA) at a flow rate of 0.5 ml/min.
4) Finally, the active fractions were rechromatographed with the same reverse-phase column in the same acetonitrile gradient containing 0.05% hexafluorobutyric acid instead of 0.1% TFA.
5) The eluate was pooled and dialyzed twice against 25 mM sodium phosphate buffer, pH 7.4.
6) The eluent was stored at −80° C.

Purification of LECT2a is shown in Table 1.

1.7 mM tetrametnylbenzidine (TMB), 0.39 mM hydrogen peroxide, 84.2 mM sodium citrate buffer (pH 5.4), 7.2% N,N'-dimethylformamide, phosphate buffered saline without calcium and magnesium (PBS(−)) and HBSS in a total volume of 200 μl per well of a 96 well-F-plate (#2-69620, available from Nunc, Denmark). Increase in absorbance at 650 nm in the reaction mixture at 37° C. was measured with an automatic analyzer LFA-096 (trade name, available from Japan Spectroscopic Co., Tokyo, Japan) at 30 sec intervals. One unit was defined as the activity producing an increase of 1.0 in absorbance at 650 nm/min/ml of original MPO preparation.

TABLE 1

Purification of LECT2a from SKW-3

| Purification steps | Volume (ml) | Activity (CTU) | Protein (mg) | Specific Activity (CTU/mg) |
|---|---|---|---|---|
| Culture fluid | 7,000 | $1.0 \times 10^7$ | 47,200 | 211 |
| CM-Sepharose CL6B eluate | 280 | $7.7 \times 10^6$ | 3,400 | 2,265 |
| DEAE-Sepharose CL6B pass-through | 300 | $7.0 \times 10^6$ | 1,800 | 3,888 |
| CM-Sepharose CL6B fraction | 4 | $2.4 \times 10^4$ | 3.6 | 6,667 |
| Reverse phase (5TMS-300) fraction* | 2 | $2.1 \times 10^4$ | 0.068 | $6.2 \times 10^5$ |

*This step represents the results of two chromatograms in different conditions.

Determination of Molecular Size of LECT2a

Molecular size of LECT2a was determined by Tricin-SDS-PAGE with 16.5% monoacrylamide-bisacrylamide:3% bis/monoacrylamide containing bis. The result is shown in FIG. 1. This result indicates that the molecular size of LECT2a is about 16 kDa.

1. Neutrophil Activation

Hanks' balanced salt solution (HBSS) contained 0.4 g KCl, 8 g NaCl, 0.15 g $KH_2PO_4$, 0.29 g $Na_2HPO_4$—$7H_2O$, and 1 g glucose in 1 liter DDW.

1) Chemotactic Activity for Neutrophils

The sample for assay was placed into the lower compartment of a Boyden chamber, and a 3.0 μm filter (Millipore, trade name, available from Bedford, Mass.) was placed on it. Then human neutrophils suspended ($2 \times 10^6$ cells/ml) in medium were placed on the filter in the upper compartment for the chemotaxis assay. The chambers were then incubated for 35 min at 37° C. in a 5% $CO_2$ humidified atmosphere. The leading front distance of the cells from the surface of the filter was the mean value of the five microscopic fields. The chemotactic unit (CTU) was calculated by three parameters; fMet-Leu-Phe (FMLP, 10 nM)-stimulated maximal migration (FM), minimal migration without the chemotactic factor, termed random migration (RM), and migration induced by the sample (SM). CTU was defined as 100× (SM−RM)/(FM−RM). In the protein purification of LECT2a, the total CTU in each purification step was calculated by multiplying the dilution of the sample for 50 CTU in the dilution-activity curve. The value of $ED_{50}$ represents the concentration of chemotactic protein at half maximum-activity in the dose-response curve.

2) Release of Lysosomal Proteins (Enzymes)

After being preincubated at a concentration of $2 \times 10^6$ neutrophils/ml of HBSS for 10 min at 37° C., neutrophils were mixed with a solution, which contained LECT2a with 0.005% BSA in the presence or absence of cytochalasin B (5 μg/ml) and FMLP (100 nM).

a) Measurement of MPO Activity

MPO activity was assayed as follows. The reaction mixture consisted of neutrophil supernatant or cell homogenate, b) Measurement of β-glucuronidase (BGL) Activity BGL activity in supernatant and cell homogenate was assayed as follows. The reaction mixture consisted of neutrophil supernatant or cell homogenate, 1 mM 4-methylumbelliferyl-β-D-glucuronide, 0.05% Triton X-100 and 0.1 M sodium acetate buffer (pH 3.5) in a total volume of a 40 μl in a 96 well-F-plate was incubated for 30 min at 37° C. A termination buffer (50 mM sodium glycine buffer (pH 10.4) containing 5 mM EDTA-disodium) was added. Fluorescence intensity was measured by an automatic fluorescence analyzer LFA-96F (trade name, available from Japan Spectroscopic Co., Tokyo, Japan) with wavelengths at 365 nm for excitation and 405 nm for emission. One unit of BGL activity was defined as the activity liberating 1 pmol of 4-methylumbelliferone/min/ml of the original BGL preparation.

c) Determination of Lactoferrin (LF)

LF protein in supernatant and cell homogenate was measured as follows. A 100 μl of 0.05% goat antiserum to human LF antibody diluted with reagent dilution buffer, 0.1% BSA in PBS(−) (pH 7.4), was transferred to a 96 well-F-plate overnight at 4° C. After the plate was washed three times with PBS(−) containing 0.05% Tween-20 washing buffer, 100 μl of diluted supernatant or cell homogenate was added to the plate. After being kept for 30 min at room temperature, the plate was washed with the washing buffer three times, then a 100 μl of 0.1% rabbit antiserum to human LF was added to the plate. After being kept for 30 min at room temperature, the plate was washed three times with the washing buffer, and treated with a 100 μl of 0.025% a peroxidase-labeled goat anti-rabbit Ig G. The plate was kept for 30 min at room temperature, washed three times with the washing buffer, and treated with 200 μl of enzyme substrate in 0.05 M citrate buffer (pH 5.0) containing 0.025% hydrogen peroxide and 0.04% of o-phenylenediamide-dihydrochloride for about 20 min at room temperature in the dark. Then, a 50 μl of 2.5 N sulfuric acid was added to the plate to terminate the reaction, subsequently absorbance at 490 nm was measured with an automatic analyzer LFA-096, and LF content in supernatant or cell homogenate was determined.

3) Superoxide Production of Neutrophils

Superoxide production was measured as follows. Neutrophils suspension ($2 \times 10^6$ cells/ml, 100 μl) and 0.066 mM of ferri cytochrome c were mixed in 96 well-F-Plate and kept for approximately 2 min. A sample, cytochalasin B (5 μg/ml) and FMLP (1000 nM) were subsequently added to the suspension and left standing for approximately 30 sec at 37° C. Superoxide production was determined by measuring the increase in absorbance at 546 nm at 0.269 min interval using the automatic analyzer LFA-096.

4) Adhesion of Neutrophils

Neutrophils adhesion was measured as follows. Neutrophils suspension ($2 \times 10^6$ cells/ml, 100 μl) was inoculated into a glass-rubber chamber. The sample containing LECT2a (10 μl), and FMLP ($10^{-11}$ to $10^{-5}$) were added to the chamber in a total volume of 150 μl. The chamber was incubated for 15 min at 37° C. in a $CO_2$ incubator. After the incubation, non-adherent cells were aspirated and the cell concentration was counted. Then the slide chamber was fixed with ethanol and stained with safulanin.

5) Membrane Fluidity of Neutrophils

After neutrophils and FITC-labeled succinyl concanavalin-A (FS-ConA) were incubated for 10 min at 37° C., PBS(-) was added to the mixture. The FS-ConA labeled neutrophils were prepared with HBSS at a concentration of $10^6$ cells/ml, and then plated into a slide chamber. A solution of the leukocyte activating factor (10 μl) and FMLP (10 nM) was added to the cell suspension in a total volume 150 μl. The cell suspension was observed through an image analyzer (IMRAS) connected with Nikon inverted microscope. The membrane fluidity was analyzed with IMRAS processor. Five activities of neutrophils carried out using the above procedures are summarized in Table 2.

TABLE 2

Summary of neutrophil activation with LECT2a

| Concentration of LECT2a | Release of Proteins (% Release*) | | | Superoxide Production | Cell Adhesion (%) | Membrane Fluidity |
| --- | --- | --- | --- | --- | --- | --- |
| (nM) | MPO | BGL | LF | (nmoles/ml) | | (sec/μm) |
| 0 | 24 | 45 | 14 | 12 | 88 | 36 |
| 0.01 | 25 | 43 | 14 | 14 | 88 | 38 |
| 0.1 | 27 | 46 | 17 | 13 | 86 | 33 |
| 1 | 26 | 46 | 16 | 12 | 89 | 36 |
| 10 | 24 | 44 | 17 | 11 | 90 | 39 |
| 100 | 25 | 44 | 16 | 15 | 93 | 42 |
| 1000 | 28 | 49 | 20 | 18 | 92 | 49 |
| 10000 | 35 | 52 | 25 | 25 | 95 | 53 |

*% Release = 100 × S/ (S + H).
S = extracellular enzyme activity (or protein content).
H = intracellular remained enzyme activity (or protein content).

2) Chemotactic Activity of Monocytes and Lymphocytes

The procedures were almost the same as those for neutrophils, except a 5 μm Millipore filter was instead of a 3 μm, and except for a 75-min incubation instead of a 35-min incubation. The concentration of LECT2a given $ED_{50}$ were 220 nM in monocytes and 430 nM in lymphocytes, respectively.

2. Amino Acid Sequencing of Purified LECT2a

Ten micrograms of pyridyl ethylated LECT2a were digested with TPCK-trypsin (trade name, available from Worthington Biochemicals, Freehold, N.J.) (E/S =1:50, w/w) in 1.5 ml of 50 mM Tris-HCl buffer, pH 8.0, containing 1 mM $CaCl_2$ at 37° C. for 8 hours. Peptides from the proteolytic digestion were separated by reverse-phase HPLC on a wide pore ODS column (0.46×25 cm) (trade name, available from J.T. Baker Research Products, Phillipsburg, N.J.) with an acetonitrile gradient in 0.1% TFA. Automatic amino acid sequence analysis was carried out with a gas phase amino acid sequencer model 477A (trade name, available from Applied Biosystems, Foster City, Calif.).

3. Cloning of LECT2b and Determination of Nucleotide sequence of the cloned LECT2b Polyadenylated [poly(A)$^+$] RNA was prepared. For cloning, Poly(A)$^+$ RNA (5 μg) from SKW-3 treated with PHA-P (50 μg/ml) was used as a template for synthesis of single-stranded cDNA using SuperScript™ reverse transcriptase (trade name, available from BRL, Grand Island, N.Y.). Six 17-mer oligonucleotides for the amino acid sequences WAIICA (5'-oligonucleotide) were synthesized and four for HIENCD (3'-oligonucleotide) were synthesized. The 5'- and 3'-oligonucleotide sets were each used to prime the amplification of 45 ng of SKW-3 cDNA by PCR, which was carried out for 40 cycles at 94° C. for 1 min, 55° C. for 2 min, and 72° C. for 1 min in a 50-μl reaction buffer. The amplified PCR products were separated on an agarose gel, blotted onto a Hybond-N$^+$ nylon membrane (trade name, available from Amersham, Buckinghamshire, England), and subjected to hybridization with an internal nucleotide probe GATGTC/GCTA/GTGCTCT/CGATGGC/GTCT/CACT/AGC/GTATGCT/CTT (Sequence ID No: 8) corresponding to the amino acid sequence DVLCSDG-STVYAP. The PCR product detected by Southern hybridization was cloned into pUC19.

The PCR product was subjected to nucleotide sequence analysis by the dideoxynucleotide chain-termination method (available from United States Biochemicals, Cleveland, Ohio). A λgt10 library was constructed from liver mRNA and $1.3 \times 10^6$ independent clones were screened. Twelve positive clones were isolated and classified into two types by restriction endonuclease analysis. The sequence analysis of the longest clones of each type suggested that the two types of clone would be derived from an identical gene which had two poly(A)$^+$ signals. The nucleotide sequence analysis revealed that the deduced amino acid sequences were 86% homologous to the LECT2a amino acid sequence.

4. Construction of the Plasmid Expressing a LECT2b-fusion Protein

The cDNA fragments of LECT2b, which contained a EcoRI site at 5'-end and a HindIII site at 3'-end, were amplified by PCR with 5'-primer GGCGAATTCGAAAAC-CTGTATTTTCAGGGGCCCTGGGCTAATATATG (Sequence ID No: 9) and 3'-primer CGCAAGCTTTTA-CAGGTATGCAGTAG (Sequence ID No: 10) for 25 cycles at 94° C. for 1 min, 55° C. for 2 min, and 72° C. for 3 min. The LECT2b cDNAs digested with EcoRI and HindIII restriction endnucleases were ligated into the EcoRI/HindIII site of pMAL™-c expression vector (trade name, available from Biolab Inc.). This plasmid was named pMAL-TEV-LECT2b. Important features of this plasmid are that the recombinant fusion protein is inducible by IPTG treatment and has the recognition site of TEV protease (derived from Tabacco Etch Virus) between maltose-binding protein and LECT2b protein.

Induction of pGEX-Xa-LECT2b

The cDNA fragments of LECT2b, which contained a BamHI site at 5'-end and at 3'-end, were amplified by PCR with 5'-primer GCGGGATCCCCGGGC-CATGGGCTAATAT (Sequence ID No: 11) and 3'-primer CGCGGATCCTTACAGGTATGCAGTAG (Sequence ID No: 12) for 25 cycles at 94° C. for 1 min, 55° C. for 2 min, and 72° C. for 3 min. The LECT2b cDNAs digested with BamHI restriction endnucleases were ligated into the BamHI site of pGEX-3X expression vector (available from Pharmacia Inc.). This plasmid was named pGEX-Xa-LECT2b. Important features of this plasmid are that the recombinant fusion protein is inducible by IPTG treatment and has the recognition site of Xa protease between Glutation-S-transferase and LECT2b protein.

5. Transformation of *E. coli* by the Vector Expressing Recombinant LECT2b

*E. coli* JM109 was transformed by pMAL-TEV-LECT2b, and resulted transformants were confirmed by DNA sequencing. The Mal-LECT2b strain (deposited at the NATIONAL INSTITUTE OF BIOSCIENCE AND HUMAN-TECHNOLOGY, Agency of Industrial Science and Technology, 1-3, Higashi 1-chome, Tsukuba-shi, Ibaraki-ken 305, Japan under FERM P-14669 and transferred to international deposition under FERM BP-5302 on Nov. 24, 1995 under the Budapest Treaty), which had the expression plasmid coding the precise LECT2b protein sequence, was selected.

Expression of LECT2b Protein in Animal Cells

The pOLECT2b plasmid was digested with BglII and carried out by self-ligation. The 5'-side of cDNA in the resulted plasmid was deleted until up 5-bp from the predicted ATG by Exonuclease III. The deleted DNA was treated with klenow fragment and was ligated with PstI linkers. This deleted plasmid was digested with PstI and BglII, and PstI-BglII fragment of LECT2b was cloned into the PstI/BamHI site of pcDSRα296. This expression vector (pSRαLECT2b) was transfected into CHO cells grown to about 50% confluence. Then, stable transformant cells (C1D8-1) (deposited at the NATIONAL INSTITUTE OF BIOSCIENCE AND HUMAN-TECHNOLOGY, Agency of Industrial Science and Technology, 1-3, Higashi 1-chome, Tsukuba-shi, Ibaraki-ken 305, Japan under FERM P-14668 and transferred to international deposition under FERM BP-5301 on Nov. 24, 1995 under the Budapest Treaty) producing a large amount of LECT2b was obtained.

Determination of Molecular Size of LECT2b

The recombinant LECT2b protein expressed in CHO cells was metabolically labeled with $^{35}$S-methionine and the proteins were detected by SDS-PAGE. The bands of LECT2b were detected in about 16 kDa in the position. These results indicate that molecular size of LECT2b was identical to that of LECT2a.

Determination of the Activity

The activity of the leukocyte activating factor LECT2b was determined by the same procedures as those described for LECT2a. The results are shown in Table 3.

TABLE 3

Summary of neutrophil activation with LECT2b

| Concentration of LECT2b (nM) | Release of MPO (% Release*) | | | Superoxide Production (nmoles/ml) | | |
|---|---|---|---|---|---|---|
| | none | CB | CB + FMLP | none | CB | CB + FMLP |
| 0 | 14.6 | 10.3 | 38.4 | 0 | 0 | 16.5 |
| 0.01 | 11.8 | 8.9 | 37.1 | -1.7 | 0 | 17.7 |
| 0.1 | 11.8 | 8.9 | 37.5 | 0 | 0 | 16.3 |
| 1 | 13.2 | 10.2 | 33.9 | 1.2 | 0.6 | 18.3 |
| 10 | 12.6 | 10.0 | 33.9 | 0.7 | 0.8 | 22.9 |
| 100 | 12.7 | 10.9 | 36.9 | 0 | 0 | 21.9 |
| 1000 | 15.3 | 13.6 | 44.0 | 1.0 | 1.6 | 22.9 |
| 10000 | 21.8 | 17.2 | 55.3 | 0 | 1.0 | 20.3 |

*% Release = 100 × S/ (S + H).
S = extracellular MPO activity.
H = intracellular remained MPO activity.

LECT2a and LECT2b proteins are grouped in a novel cytokine/interleukin which activate immune cells. This shows that these proteins are useful for diagnosis, therapy and prediction of cancer by their immune reaction. Further, these proteins will be employed for cancer therapy. On the other hand, activation of neutrophils and other inflammation cells by these proteins will have relationships to chronic disease, suggesting that these proteins will be widely used for diagnosis, therapy and detection of disorders of the cytokine network.

We claim:

1. Isolated DNA encoding LECT2b amino acid sequence in the order shown in Sequence ID NO: 6.

2. Isolated DNA comprising the nucleotide sequence set forth in Sequence ID NO: 7.

3. Recombinant plasmids containing DNA encoding human LECT2b having an amino acid sequence shown in Sequence ID NO: 6.

4. The recombinant plasmids according to claim 3, which is plasmid pMAL-TEV-LECT2b constructed by ligation of the nucleotide sequence encoding LECT2b protein downstream of maltose-binding protein region in pMAL-c vector to induce fused protein by IPTG treatment and having a TEV protease recognition site located between maltose binding protein and LECT2b.

5. The recombinant plasmids according to claim 3, which is plasmid pGEX-Xa-LECT2b constructed by ligation of the nucleotide sequence encoding LECT2b protein downstream of glutathione-S-transferase region in pGEX vector to induce fused protein by IPTG treatment and having a Xa protease recognition site located between glutathione-S-transferase and LECT2b.

6. The recombinant plasmids according to claim 3, wherein the nucleotide sequence encoding human LECT2b is regulated with SRα promotor.

7. Transformed cells transfected with plasmid constructs which contain human LECT2b gene encoding amino acid sequence shown in the sequence ID. NO: 6.

8. The transformed cells according to claim 7, wherein the transformed cells are obtained by transforming into the cells selected from the group consisting of *E. coli,* yeast, insect cells, Chinese hamster CHO cells, monkey CVI cells, monkey CVI/293 cells, mouse fibroblast, mouse C127 cells, mouse 3T3 cells, mouse L-929 cells, human HeLa cells and human SKW-3 cells.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 54 amino acids
      (B) TYPE: amino acid
      (C) STRANDEDNESS: single strand
      (D) TOPOLOGY: linear (ii) MOLECULE TYPE: protein (v) FRAGMENT TYPE: N-terminal fragment (vi) ORIGINAL SOURCE:
      (A) ORGANISM: human
      (F) TISSUE TYPE: T-cell derived leukemia cells (x) PUBLICATION INFORMATION:
      (A) AUTHORS: Kazuo SUZUKI et al.
      (B) TITLE: NOVEL ACTIVATING FACTOR OF LEUKOCYTES
      (K) RELEVANT RESIDUES IN SEQ ID NO:1: FROM 1 to 54

(xi) SEQUENCE DESCRIPTION: SEQ ID NO:1:

Gly Pro Trp Ala Ile Ile Cys Ala Gly Lys Ser Ser Asn Glu Ile Arg
1              5              10            15

```
Thr Cys Asp Gly His Gly Cys Gly Gln Tyr Thr Ala Gln Arg Asn Gln
              20                  25                  30

Lys Leu His Gln Gly Val Asp Val Leu Cys Ser Asp Gly Ser Thr Val
         35                  40                  45

Tyr Ala Pro Phe Xaa Gly
      50

(2) INFORMATION FOR SEQ ID NO: 2:

(i) SEQUENCE CHARACTERISTICS:
         (A) LENGTH:  10 amino acids
         (B) TYPE: amino acid
         (C) STRANDEDNESS: single strand
         (D) TOPOLOGY: linear (ii) MOLECULE TYPE: protein (v) FRAGMENT TYPE: intermediate fragment (vi) ORIGINAL SOURCE:
         (A) ORGANISM: human
         (F) TISSUE TYPE: T-cell derived leukemia cells (x) PUBLICATION INFORMATION:
         (A) AUTHORS: Kazuo SUZUKI et al.
         (B) TITLE: NOVEL ACTIVATING FACTOR OF LEUKOCYTES
         (K) RELEVANT RESIDUES IN SEQ ID NO:2: FROM 1 to 10

(xi) SEQUENCE DESCRIPTION: SEQ ID NO:2:

Ile Met Gly Gln Glu Lys Pro Tyr Lys Asn
 1               5                  10

(2) INFORMATION FOR SEQ ID NO: 3:

(i) SEQUENCE CHARACTERISTICS:
         (A) LENGTH:  9 amino acids
         (B) TYPE: amino acid
         (C) STRANDEDNESS: single strand
         (D) TOPOLOGY: linear (ii) MOLECULE TYPE: protein (v) FRAGMENT TYPE: intermediate fragment (vi) ORIGINAL SOURCE:
         (A) ORGANISM: human
         (F) TISSUE TYPE: T-cell derived leukemia cells (x) PUBLICATION INFORMATION:
         (A) AUTHORS: Kazuo SUZUKI et al.
         (B) TITLE: NOVEL ACTIVATING FACTOR OF LEUKOCYTES
         (K) RELEVANT RESIDUES IN SEQ ID NO:3: FROM 1 to 9

(xi) SEQUENCE DESCRIPTION: SEQ ID NO:3:

Ile Ser Gly Gly Gly Phe Cys Ile Lys
 1               5

(2) INFORMATION FOR SEQ ID NO: 4:

(i) SEQUENCE CHARACTERISTICS:
         (A) LENGTH:  5 amino acids
         (B) TYPE: amino acid
         (C) STRANDEDNESS: single strand
         (D) TOPOLOGY: linear (ii) MOLECULE TYPE: protein (v) FRAGMENT TYPE: intermediate fragment (vi) ORIGINAL SOURCE:
         (A) ORGANISM: human
         (F) TISSUE TYPE: T-cell derived leukemia cells
```

(x) PUBLICATION INFORMATION:
            (A) AUTHORS: Kazuo SUZUKI et al.
            (B) TITLE: NOVEL ACTIVATING FACTOR OF LEUKOCYTES
            (K) RELEVANT RESIDUES IN SEQ ID NO:4: FROM 1 to 5

(xi) SEQUENCE DESCRIPTION: SEQ ID NO:4:

Tyr Lys Gly Ser Ile
 1               5

(2) INFORMATION FOR SEQ ID NO: 5:

(i) SEQUENCE CHARACTERISTICS:
            (A) LENGTH: 20 amino acids
            (B) TYPE: amino acid
            (C) STRANDEDNESS: single strand
            (D) TOPOLOGY: linear (ii) MOLECULE TYPE: protein (v) FRAGMENT TYPE: intermediate fragment (vi) ORIGINAL SOURCE:
            (A) ORGANISM: human
            (F) TISSUE TYPE: T-cell derived leukemia cells (x) PUBLICATION INFORMATION:
            (A) AUTHORS: Kazuo SUZUKI et al.
            (B) TITLE: NOVEL ACTIVATING FACTOR OF LEUKOCYTES
            (K) RELEVANT RESIDUES IN SEQ ID NO:5: FROM 1 to 20

(xi) SEQUENCE DESCRIPTION: SEQ ID NO:5:

Val Tyr Pro Gly Ile Gln Ser His Ile His Ile Glu Asn Xaa Asp Leu
 1               5                  10                  15

Ser Asp Pro Thr
            20

(2) INFORMATION FOR SEQ ID NO: 6:

(i) SEQUENCE CHARACTERISTICS:
            (A) LENGTH: 151 amino acids
            (B) TYPE: amino acid
            (C) STRANDEDNESS: single strand
            (D) TOPOLOGY: linear (ii) MOLECULE TYPE: protein (v) FRAGMENT TYPE: intermediate fragment (vi) ORIGINAL SOURCE:
            (A) ORGANISM: human
            (F) TISSUE TYPE: T-cell derived leukemia cells (x) PUBLICATION INFORMATION:
            (A) AUTHORS: Kazuo SUZUKI et al.
            (B) TITLE: NOVEL ACTIVATING FACTOR OF LEUKOCYTES
            (K) RELEVANT RESIDUES IN SEQ ID NO:6: FROM 1 to 151

(xi) SEQUENCE DESCRIPTION: SEQ ID NO:6:

Met Phe Ser Thr Lys Ala Leu Leu Ala Gly Leu Ile Ser Thr Ala
 1               5                  10                  15

Leu Ala Gly Pro Trp Ala Asn Ile Cys Ala Gly Lys Ser Ser Asn Glu
                20                  25                  30

Ile Arg Thr Cys Asp Arg His Gly Cys Gly Gln Tyr Ser Ala Gln Arg
            35                  40                  45

Ser Gln Arg Pro His Gln Gly Val Asp Val Leu Cys Ser Ala Gly Ser
        50                  55                  60

Thr Val Tyr Ala Pro Phe Thr Gly Met Ile Val Gly Gln Glu Lys Pro
65                  70                  75                  80

```
Tyr Gln Asn Lys Asn Ala Ile Asn Asn Gly Val Arg Ile Ser Gly Arg
            85                   90                   95

Gly Phe Cys Val Lys Met Phe Tyr Ile Lys Pro Ile Lys Tyr Lys Gly
           100                 105                 110

Pro Ile Lys Lys Gly Glu Lys Leu Gly Thr Leu leu Pro Leu Gln Lys
           115                 120                 125

Val Tyr Pro Gly Ile Gln Ser His Val His Ile Glu Asn Cys Asp Ser
    130                 135                 140

Ser Asp Pro Thr Ala Tyr Leu
145                 150
```

(2) INFORMATION FOR SEQ ID NO: 7:

(i) SEQUENCE CHARACTERISTICS:
        (A) LENGTH: 1092 nucleic acids
        (B) TYPE: nucleotides
        (C) STRANDEDNESS: single strand
        (D) TOPOLOGY: linear (ii) MOLECULE TYPE: cDNA (v) FRAGMENT TYPE: intermediate fragment (vi) ORIGINAL SOURCE:
        (A) ORGANISM: human
        (F) TISSUE TYPE: liver (ix) FEATURE: Amino acid number 58 Xaa can be Val or Ile.  When
        amino acid number 58 Xaa is Ile, RTC in the nucleotide
        Sequence ID No. 372 - 374 is ATC, instead of GTC.

(x) PUBLICATION INFORMATION:
        (A) AUTHORS: Kazuo SUZUKI et al.
        (B) TITLE: NOVEL ACTIVATING FACTOR OF LEUKOCYTES
        (K) RELEVANT RESIDUES IN SEQ ID NO:7: FROM 1 to 1092
           Specificity of the sequence
           Mark describing the specificity: 5'UTR
           Localization: 1 ... 200
           Method for determination of the specificity: P
           Mark describing the specificity: 3'UTR
           Localization: 657 ... 1092
           Method for determination of the specificity: P
           Mark describing the specificity: CDS
           Localization: 201 ... 656
           Method for determination of the specificity: P
           Mark describing the specificity: mutation
           Localization: 372 is "A" or "G"
           748 is "A" or "G"
           961 is "C" or "T"
           967 is "C" or "T"
           Method for determination of the specificity: E
           Mark describing the specificity: polyA signal
           Localization: 684 ... 689
           1060 ... 1065
           Method for determination of the specificity: E (xi) SEQUENCE DESCRIPTION: SEQ ID NO:7:

```
AAATCAAATA GCTATCCATG GAATATTAGA ACTTGACTTG CTCCATCCTC              50

TTAAACTTTT TGTGTCTCAC ACTAAAGAAA TGAGAGATGC AGAATTCTAA             100

GGCTAAATAG CTAGGAAGTA TTCATTCAAA CTTGAATATC TTCAAAGAGA             150

GTGTGGGGGC AACTCTAATC AGAGGAAGAA ACTAAAGGAA GTAAAACCAG             200

ATG TTT TCC ACC AAA GCC CTC CTT TTG                                227
Met Phe Ser Thr Lys Ala Leu Leu Leu
 1               5

GCT GGT CTG ATT TCT ACC GCA CTG GCA GGG CCA TGG GCT AAT            269
Ala Gly Leu Ile Ser Thr Ala Leu Ala Gly Pro Trp Ala Asn
 10              15                  20
```

|  |  |
|---|---|
| ATA TGT GCT GGC AAG TCT TCC AAT GAG ATC CGG ACG TGT GAC<br>Ile Cys Ala Gly Lys Ser Ser Asn Glu Ile Arg Thr Cys Asp<br>  25                      30                       35 | 311 |
| CGC CAT GGC TGT GGA CAG TAC TCT GCT CAA AGA AGT CAG AGG<br>Arg His Gly Cys Gly Gln Tyr Ser Ala Gln Arg Ser Gln Arg<br>         40                    45                    50 | 353 |
| CCT CAC CAG GGT GTG GAC RTC TTG TGC TCT GCT GGA TCT ACT<br>Pro His Gln Gly Val Asp Xaa Leu Cys Ser Ala Gly Ser Thr<br>               55                     60                    65 | 395 |
| GTG TAC GCA CCA TTC ACT GGA ATG ATT GTG GGC CAG GAG AAA<br>Val Tyr Ala Pro Phe Thr Gly Met Ile Val Gly Gln Glu Lys<br>                  70                         75 | 437 |
| CCT TAT CAA AAC AAG AAT GCT ATC AAT AAT GGT GTT CGA ATA<br>Pro Tyr Gln Asn Lys Asn Ala Ile Asn Asn Gly Val Arg Ile<br>80                       85                       90 | 479 |
| TCT GGA AGA GGT TTT TGT GTC AAA ATG TTC TAC ATT AAG CCA<br>Ser Gly Arg Gly Phe Cys Val Lys Met Phe Tyr Ile Lys Pro<br>  95                     100                   105 | 521 |
| ATT AAG TAT AAA GGT CCT ATT AAG AAG GGA GAA AAA CTT GGA<br>Ile Lys Tyr Lys Gly Pro Ile lys Lys Gly Glu Lys Leu Gly<br>      110                   115                   120 | 563 |
| ACT CTA TTG CCC TTG CAG AAA GTT TAT CCT GGC ATA CAA TCG<br>Thr Leu leu Pro Leu Gln Lys Val Tyr Pro Gly Ile Gln Ser<br>         125                    130                135 | 605 |
| CAT GTG CAC ATT GAA AAC TGT GAC TCG AGT GAC CCT ACT GCA<br>His Val His Ile Glu Asn Cys Asp Ser Ser Asp Pro Thr Ala<br>              140                      145 | 647 |
| TAC CTG<br>Tyr Leu<br>150 | 653 |
| TAAATCGAAG GCCAATGGTC AGATCTTCAA AATAAAAAGT CATCTTAAAA | 703 |
| ACCTGGATGC ATACCCTTCT CTTCAAGAAA TTTGTGTTCA CAAARGAAAA | 753 |
| ATGCATGAAG GGATGGATAC CCCATTTTCC ATGACATGAT TATTACACAT | 803 |
| TGCATGCCTG TATCAAAACA TCTCACGTAC CTCATAAACA TATACACCTA | 853 |
| TGTACCCACA AAATTTTTT AATTAAAAAA AGGAAATTTG AGTTTAAATA | 903 |
| GAAACATGAT AAATGCAAGA AAGAAAACAT TTTGATTTTA ACTCATTGTC | 953 |
| ACTCTGAYGT TCAYGTGAAC TGGTTGCTTC GGGCTCTTTG ATCTGTCACC | 1003 |
| TATGGAATCT GAGTGGTTTT ATTTTTTAGA TTTCTCAGTC CCAAAGATCT | 1053 |
| AAGATAAATA AACAAGAGAA CTTAAAAAAA AAAAAAAA | 1092 |

(2) INFORMATION FOR SEQ ID NO: 8:

(i) SEQUENCE CHARACTERISTICS:
        (A) LENGTH:   37 nucleic acids
        (B) TYPE: nucleotides
        (C) STRANDEDNESS: single strand
        (D) TOPOLOGY: linear (ii) MOLECULE TYPE: cDNA (vi) ORIGINAL SOURCE: synthesized (ix) FEATURE: S means C or G, R means A or G, Y means T or C,
         and W means T or A (x) PUBLICATION INFORMATION:
        (A) AUTHORS: Kazuo SUZUKI et al.
        (B) TITLE: NOVEL ACTIVATING FACTOR OF LEUKOCYTES
        (K) RELEVANT RESIDUES IN SEQ ID NO:1: FROM 39 to 52

(xi) SEQUENCE DESCRIPTION: SEQ ID NO:8:

```
GATGTSCTRT GCTCYGATGG STCYACWGST ATGCYTT                                37
```

(2) INFORMATION FOR SEQ ID NO: 9:

(i) SEQUENCE CHARACTERISTICS:
        (A) LENGTH: 46 nucleic acids
        (B) TYPE: nucleotides
        (C) STRANDEDNESS: single strand
        (D) TOPOLOGY: linear (ii) MOLECULE TYPE: cDNA (vi) ORIGINAL SOURCE: synthesised (x) PUBLICATION INFORMATION:
        (A) AUTHORS: Kazuo SUZUKI et al.
        (B) TITLE: NOVEL ACTIVATING FACTOR OF LEUKOCYTES (xi) SEQUENCE DESCRIPTION: SEQ ID NO:9:

```
GGCGAATTCG AAAACCTGTA TTTTCAGGGG CCCTGGGCTA ATATAT                      46
```

(2) INFORMATION FOR SEQ ID NO: 10:

(i) SEQUENCE CHARACTERISTICS:
        (A) LENGTH: 26 nucleic acids
        (B) TYPE: nucleotides
        (C) STRANDEDNESS: single strand
        (D) TOPOLOGY: linear (ii) MOLECULE TYPE: cDNA (vi) ORIGINAL SOURCE: synthesised (x) PUBLICATION INFORMATION:
        (A) AUTHORS: Kazuo SUZUKI et al.
        (B) TITLE: NOVEL ACTIVATING FACTOR OF LEUKOCYTES (xi) SEQUENCE DESCRIPTION: SEQ ID NO:10:

```
CGCAAGCTTT TACAGGTATG CAGTAG                                            26
```

(2) INFORMATION FOR SEQ ID NO: 11:

(i) SEQUENCE CHARACTERISTICS:
        (A) LENGTH: 28 nucleic acids
        (B) TYPE: nucleotides
        (C) STRANDEDNESS: single strand
        (D) TOPOLOGY: linear (ii) MOLECULE TYPE: cDNA (vi) ORIGINAL SOURCE: synthesised (x) PUBLICATION INFORMATION:
        (A) AUTHORS: Kazuo SUZUKI et al.
        (B) TITLE: NOVEL ACTIVATING FACTOR OF LEUKOCYTES (xi) SEQUENCE DESCRIPTION: SEQ ID NO:11:

```
GCGGGATCCC CGGGCCATGG GCTAATAT                                          28
```

(2) INFORMATION FOR SEQ ID NO: 12:

(i) SEQUENCE CHARACTERISTICS:
        (A) LENGTH: 26 nucleic acids
        (B) TYPE: nucleotides
        (C) STRANDEDNESS: single strand
        (D) TOPOLOGY: linear (ii) MOLECULE TYPE: cDNA (vi) ORIGINAL SOURCE: synthesised (x) PUBLICATION INFORMATION:

(A) AUTHORS: Kazuo SUZUKI et al.
(B) TITLE: NOVEL ACTIVATING FACTOR OF LEUKOCYTES (xi) SEQUENCE DESCRIPTION: SEQ ID NO:12:

CGCGGATCCT TACAGGTATG CAGTAG                                           26